United States Patent [19]

King

[11] Patent Number: 4,930,163

[45] Date of Patent: Jun. 5, 1990

[54] APPARATUS FOR SUPPORTING AN EYEGLASS FRAME LENS ASSEMBLY IN A DIVING OR PROTECTIVE MASK

[76] Inventor: Mathew B. King, 19011 East Mansfield Drive, Aurora, Colo. 80013

[21] Appl. No.: 284,909

[22] Filed: Dec. 15, 1988

[51] Int. Cl.⁵ .............................................. A61F 9/02
[52] U.S. Cl. ...................................... 2/444; 351/158; 128/201.12
[58] Field of Search ................. 2/444, 426, 10, 424; 351/158, 47, 155; 128/201.12

[56] References Cited

U.S. PATENT DOCUMENTS

| | | | |
|---|---|---|---|
| 2,905,172 | 9/1959 | Rodenhouse | 351/158 X |
| 2,962,722 | 12/1960 | Curran | 2/444 |
| 2,993,209 | 7/1961 | Monahan, Jr. et al. | 2/444 |
| 3,051,957 | 9/1962 | Chan | 2/444 X |
| 3,146,295 | 8/1964 | Roland | 2/444 X |
| 3,182,658 | 5/1965 | Klinger | 128/201.12 |
| 3,288,547 | 11/1966 | Klinger et al. | 351/155 |
| 3,563,640 | 2/1971 | Wise et al. | 351/158 |
| 3,787,113 | 1/1974 | Shedrow | 351/158 X |
| 4,023,214 | 5/1977 | Waldherr | 2/444 |
| 4,057,057 | 11/1977 | Backlund | 128/201.12 |
| 4,105,026 | 8/1978 | Hay | 128/201.12 |
| 4,349,251 | 9/1982 | Shedrow | 351/158 X |
| 4,542,965 | 9/1985 | Shedrow | 351/47 X |
| 4,711,539 | 12/1987 | Krusas et al. | 351/158 X |

*Primary Examiner*—Peter Nerbun
*Attorney, Agent, or Firm*—Timothy J. Martin

[57] ABSTRACT

An apparatus for supporting a frame lens assembly of a conventional pair of eyeglasses having a left and right temple portion within a face mask, such as a diver's scuba mask or the like, for a period of temporary use in combination with the mask. The mask having a viewing window and a tubular shroud surrounding the viewing window which includes left and right support members and pivotal attachment means for attaching the left and right support members to the left and right temple portions of the eyeglass frame assembly, respectively, and means for rotationally biasing the support members outwardly and away from one another to urge the support members into abutting relation to the shroud and to the viewing window causing the eyeglass frame assembly to be supported in a functional position within the mask.

41 Claims, 6 Drawing Sheets

APPARATUS FOR SUPPORTING AN EYEGLASS FRAME LENS ASSEMBLY IN A DIVING OR PROTECTIVE MASK

TECHNICAL FIELD

The present invention relates to an apparatus to allow the use of scuba diving and protective masks in combination with corrective eyeglasses. More specifically, the invention relates to structures for supporting the frame and lens assembly of a conventional pair of eyeglasses within a diving or protective face mask having a viewing window for use in combination with the mask.

BACKGROUND OF THE INVENTION

Persons who utilize conventional eyeglasses having ear pieces extending backward from a temple portion of the frames face considerable difficulties should they wish to utilize that eyewear in combination with a scuba diving mask, ski goggles, gas masks, or other protective masks which mount to the face or surround the head. The difficulties of utilizing such eyewear with a scuba diving face mask are most obvious as the temple pieces which pass back over the ears make it impossible for the mask to maintain an airtight seal around the eye and nose area of the face. Similar difficulties may be experienced with gas masks, where a gas tight seal must also be maintained. Problems are also presented in the use of protective masks, such as ski goggles where, while maintaining a seal against the wearer's face is less critical, retaining devices used to hold the protective mask in place against the face and the mask perimeter itself may interfere with the temple portions of the eyeglasses making it difficult to maintain both the eyeglass and protective mask in proper functional position. Similar interface problems may be encountered when using protective face shields for eye protection while operating machinery, such as grinding equipment.

Devices have been available in the prior art which are intended to allow the frame assembly of a conventional pair of eyeglasses, with the temple pieces removed, to be supported within a diving mask. However, these devices have generally been cumbersome and inconvenient to use. Many require special fittings to be provided within the mask, on the shroud or on the viewing window, during manufacture or that the mask be modified or altered after manufacture to include such special fittings before the prior art device can be used. Some prior art devices have utilized suction cups in an attempt to eliminate the need for special fittings or a modification of the mask, but these devices may loosen at an inconvenient time during use. Most prior art frame assembly support devices allow only limited adjustment of the location of the frame assembly within the mask. Further, most do not hold the frame assembly in position in a resilient manner to allow for small variations in facial contour and mask location relative to a wearer's face for comfort and effectiveness during activities undertaken while wearing the mask.

DISCLOSURE OF THE INVENTION

It is an object of the present invention to provide an apparatus for supporting a conventional eyeglass lens frame assembly within a scaba diving or protective face mask.

A further object of the present invention is to allow the position of the frame assembly to be adjusted within the mask for optimum advantage of the user.

Also, it is an object of the present invention to provide a device which will allow the frame assembly to be quickly and easily mounted within the mask, and, after use, readily removed from the mask and converted back to conventional use.

Further, it is an object of the present invention to provide a means for supporting a conventional eyeglass frame lens assembly within a scuba diving or protective mask which does not require that the mask be manufactured or modified to include special fittings.

Additionally, it is an object of the present invention to provide a versatile frame-lens support device which will support frame-lens assemblies of various shapes and sizes within a variety of face masks of different types, designs and sizes.

Yet another objective of the present invention is to support the frame-lens assembly within the face mask in a resilient manner which will allow for variations in facial contour and for small, unavoidable shifting of the mask relative to the user's face during activities for which the mask is worn.

In accordance with these objectives in the eyeglass support apparatus of the present invention, a left and right support member each have a base which is for contacting an interior surface of the viewing window of a scuba diving or protective mask within which the eyeglass frame-lens assembly is to be supported. A left and right adjustment member are each adjustable fastened in abutting relation to the left and right support members, respectively, by a nut and bolt set. The shaft of the bolt passes through an elongate channel in each of the support member and the adjustment member. The channels of the support member and the adjustment member are arranged so that their longitudinal axes form an angle relative to one another to allow both rotational and two-dimensional linear adjustment of the adjustment member relative to the support member when the nut and bolt set is loosened. The adjustment member position relative to the support member may then be fixed by tightening the nut and bolt set.

In a preferred embodiment, the left and right adjustment members each have a support end with a C-shaped opening and a shaft mounted traversely across the mouth of the opening. A left and right adapter member each have a support end with an aperture through which the shaft of the left and right adjustment member, respectively, passes so the adapter member is confined within the opening in a sliding fit on the shaft. A first and second, partially compressed coil spring surround each shaft and are separated by the support end of the adapter member so that the support end of the adapter member is resiliently biased to a location on the shaft at the center of the mouth of the C-shaped opening of the adjustment member.

Each adapter member also has a frame assembly engagement end with an upper and lower extension portion defining an open channel therebetween. The upper and lower extension portions of each adapter member have coaxial apertures, and the aperture of the upper extension portion is provided with an internal thread for cooperative engagement by external threads of a pin member having a hinge pin extended portion. Thus, once the temple pieces are removed from a conventional eyeglass frame lens assembly, the left and right temple hinge portion of the frame may be placed in the channel of the left and right adapter member, respectively, between the upper and lower extension members and the pin member may be threaded into the upper extension member with its hinge pin portion passing through the hinge pin hole of the frame assembly and on through the aperture of the lower extension member to retain the temple hinge portion of the frame assembly within the channel of the adapter member.

The first and second coil spring surrounding the tranverse shaft of the adjustment members are tensively coiled and provided with bent end portions which engage and resiliently, rotationally bias the adjustment members relative to the adapter members so that, when the left and right adapter members are in engagement with the left and right temple hinge portion of the frame assembly, respectively, and extending in a forward direction from the frame-lens assembly, the left and right support members are biased outward and away from one another. Thus, when the frame-lens and support device combination is positioned within the face mask, the support members are urged into abutting relation with the shroud portion of the mask and the eyeglass frame assembly will be supported in a position to assist the mask and eyeglass wearer.

In an alternative embodiment, spring bias is provided by a spring elements lying along the longitudinal axes of the support assemblies and attached at one end to an adapter member and at the other end to an adjustment member.

In another alternative embodiment, for use with a face protective mask which does not have a surrounding shroud, the base portion of the support members may be provided with releasable attachment means for attachment to the interior surface of the viewing window of the protective mask. The releasable attachment means may comprise a hook and loop fastener system, with the face shield portion mounted on an adhesive strip which can be applied to the interior surface of the face shield for engagement of the base portion of the support member.

These and other features and advatages of the present invention will become apparent upon consideration of the following specification and claims, together with the accompanying drawings.

DETAILED DESCRIPTION OF THE INVENTION

Figure 1:
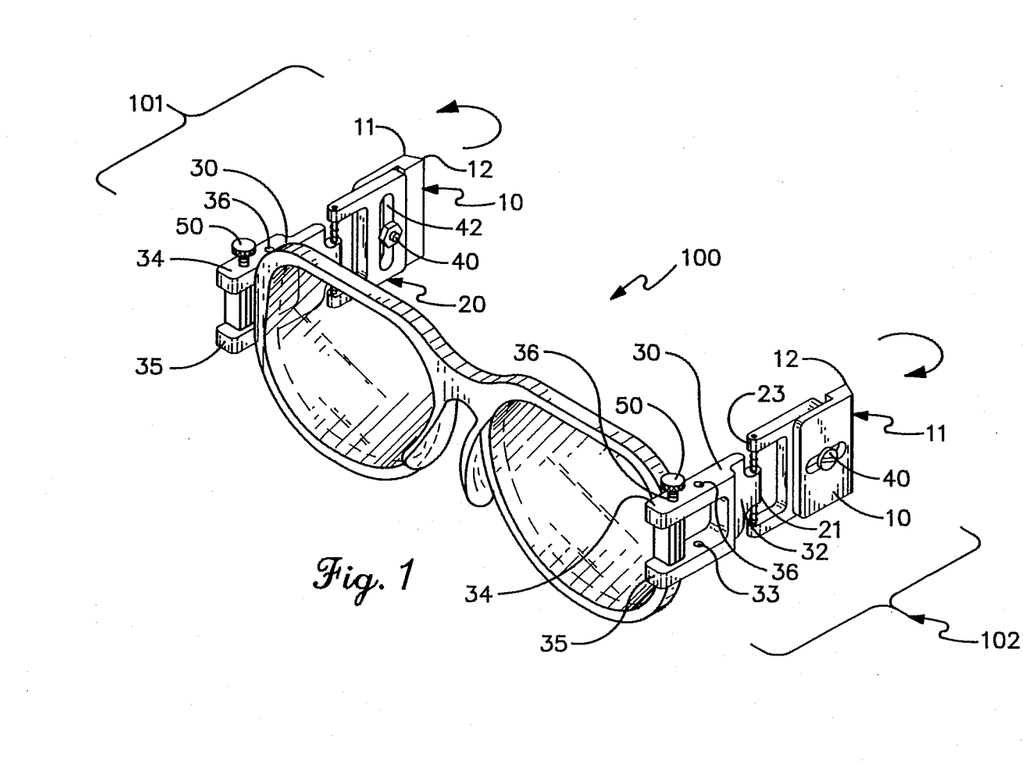
FIG. 1 is a perspective view of a conventional eyeglass frame and lens assembly with the support apparatus of the present invention attached to its left and right temple hinge portions.

FIG. 1 is a perspective view of an exemplary frame-lens assembly support apparatus 100 comprising a preferred embodiment of the present invention, shown in supporting engagement with the frame and lens assembly 10 of a conventional pair of eyeglasses. Frame assembly support apparatus 10 generally comprises a right and left support assembly 101, 102, each of which includes a support member 10, adjustment member 20 and adapter member 30. The support members 10, adjustment members 20 and adapter members 30 of left and right support assemblies 101, 102 may be made of any suitable material, for example metal or plastic. Where the support apparatus is to be used in an aquatic environment preferably be fabricated of non-corrosive materials such as plastic or stainless steel.

Support members 10 each have a base end 11 including a contact portion 12. Base ends 11 of the support members 10 of the exemplary preferred embodiment 100 are planer and form an acute supporting edge 12 at the inside of support member 10, but might be of another convenient shape, for example, cylindrical or pointed with a central apex. In the case of a cylindrical shape, support portion 12 would be a longitudinal element of the cylindrical surface. The angle formed by planar base ends 11 may be any suitable angle, and may be adjusted so that the entire base surface is included in contact portion 12.

Adjustment members 10 of the exemplary eyeglass frame assembly support apparatus 100 are adjustably fastened in abutting relation to support members 10 by nut and bolt sets 40 which pass through elongated channels 41 and support members 40 and elongated channels 42 in adjustment members 20. Support members 41 run in a direction parallel to a longitudinal axis of support assemblies 101, 102 and adjustment member channels 42 run in a direction generally perpendicular to those longitudinal axes so that, when nut and bolt sets 40 are loosened, support members 10 and adjustment members 20 may be adjusted relative to one another rotationally and two-dimensionally. Once support members 10 and adjustment members 20 are adjusted to their desired relative positions, nut and bolt sets 40 may be tightened to firmly clamp and fix support members 10 and adjustment members 20 in the desired adjusted relation.

Adjustment member 20 of the preferred exemplary embodiment has a "C" shaped opening 21 in its support end. A shaft 22 is mounted transversely across a mouth of the opening and passes through an aperture 31 provided in the support end 32 of adapter member 30. Aperture 31 is sized to provide a sliding fit about shaft 22 and partially compressed upper and lower coil springs 46, 47 surround shafts 22 above and below adapter members 30 so that support ends 32 of adapter members 30 are resiliently constrained at the center of the mouth of "C" shaped openings 21 on shafts 22. Coil springs 46, 47 are preferably fabricated of stainless steel, but may be formed of any suitably elastic, preferably non-corrosive, material.

Channels 33 are formed in the frame assembly engagement end of adapter members 30 by upper and lower extension portions 34, 35 which have co-axial aperture 36, 37 formed therein. As may be more clearly seen in FIG. 2, aperture 36 of upper extension portion 34 of the exemplary embodiment is threaded to receive a threaded portion 51 of pin member 50. Pin member 50 is preferably constructed with a large knurled head portion 52 and a lower hinge pin portion 53. Lower hinge portion 53 is suitably sized to pass through the hole in a hinge fitting of the temple portion of conventional eyeglass frame-lens assembly 1 when both temple pieces are removed and is of sufficient length to enter the aperture 37 of the lower extension portion when pin member 50 is threaded into the upper aperture 36. Thus, once the temple pieces are removed from frame assembly 1, the hinge fittings of the left and right temple portions of the frame assembly may be inserted into channels 33 of the adapter members 32 of left and right support members 101, 102, respectively, and pin members 50 threaded firmly into apertures 36 of upper extension portions 34 of adapter members 30 with hinge pin portions 53 of pin members 50 passing through the holes of the hinge fittings of frame assembly 1 and apertures 37 of lower extension portions 35 of the adapter members 30 to secure frame assembly 1 to support members 101, 102. Multiple apertures may be provided in extension portions 34, 35 to allow engagement of frame assemblies of different sizes and shapes.

Figures 2, 3, 5:
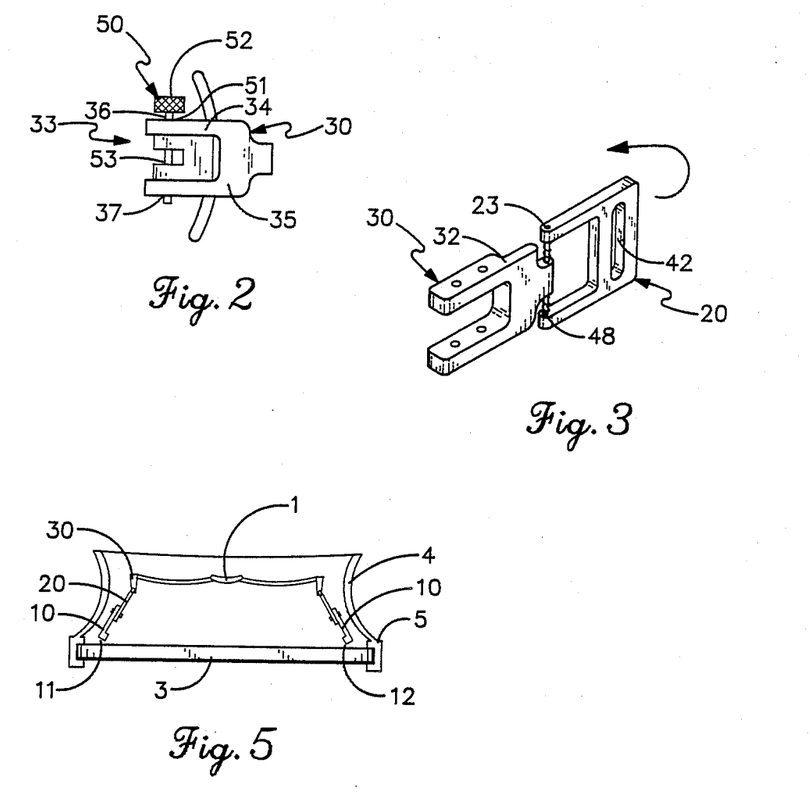
FIG. 2 is a side elevation of a frame and lens assembly of a conventional pair of eyeglasses with the temple hinge portion engaged in the channel of the adapter member of the present invention by the hinge pin portion of the pin member.
FIG. 3 is a perspective view showing the arrangement of resilient coil springs and their end engagement of an adapter member and an adjustment member to provide an outward rotational bias of the adjustment member.
FIG. 5 is a top, plan view of a convention eyeglass frame and lens assembly supported within a scuba diving mask by the support apparatus of the present invention.

As may be more easily seen in FIG. 3, coil springs 46, 47 have bent or tabbed ends 48 engage adapter members 30 and adjustment members 20, and are tensively coiled about transverse shafts 22 to provide a rotational bias about shafts 22 in such a direction that, when left and right support assemblies 101, 102 are engaged with the left and right temple portions of eyeglass assembly 1, respectively, and extend forward from frame assembly 1, support members 20 of left and right support assemblies 101, 102 are urged by coil springs 46, 47 to rotate outwardly and away from one another as indicated by the arrows in FIG. 1.

Figure 4:
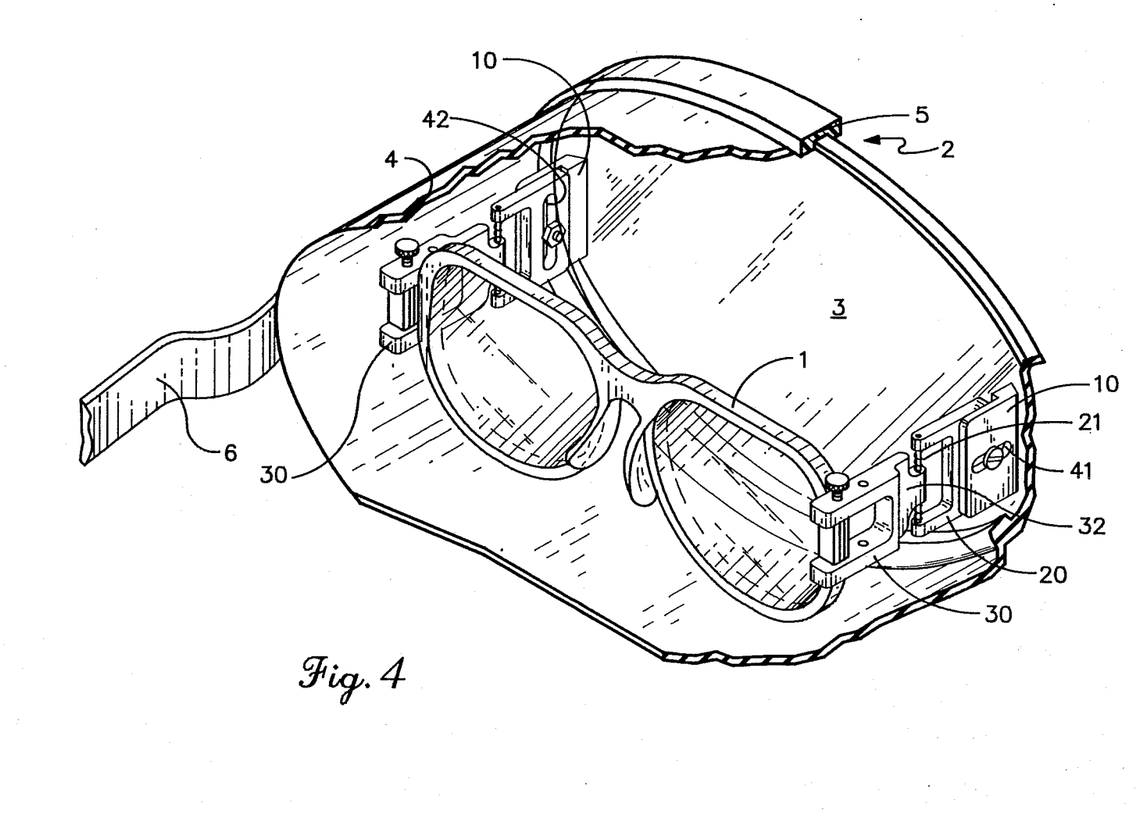
FIG. 4 is a partially cut-away perspective view of a conventional eyeglass frame and lens assembly as it would be supported in a scuba mask by a support apparatus comprising the preferred embodiment of the present invention.

The manner in which frame assembly 1 is supported within a scuba diving mask 2 by the exemplary embodiment of the frame-lens assembly support apparatus is illustrated in FIG. 4. When it is desired to use frame assembly 1 in combination with mask 2, the temple pieces of the conventional eyeglasses are first removed and the hinge fittings of the frame assembly are engaged in the adapter members 30 by placing the left and right hinge fittings in the channels 33 and threading pin members 50 to apertures 36 of upper extension portions 34 of left and right support assemblies 101, 102, respectively. Support members 30 of support assemblies 101, 102 are then held so as to extend directly forward from frame assembly 1 and frame assembly 1, together with the support apparatus 100, are inserted into shroud 4 of scuba mask 2 until base ends 11 of support members 10 are immediately adjacent to viewing window 3, and support assemblies 101, 102 are released. As can best be seen in FIG. 5 upon release, support members 10 are urged outwardly and away from one another by spings 46, 47 as indicated by the arrows in FIG. 5 so that the outer surfaces of support members 10 are biased into abutment with shroud 4 of scuba mask 2 and the contact portions 12 of the bases 11 of support members 10 are held in contact with the interior surface of the viewing window 3. With proper adjustment of the relation between support members 10 and adjustment members 20, when mask 2 is urged against the divers face by elastic straps 6, frame assembly 1 will be in a functional viewing position in proper contact with the divers nose when the combination is worn. The resilient biasing action of springs 46, 47 will allows for movement of the mask 2 relative to the divers face and changes in facial contour during diving activities while the mask is being worn.

Figure 6A:
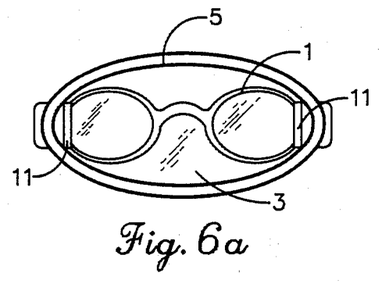
FIG. 6a is a front elevation of a frame and lens assembly of a conventional pair of eyeglasses supported in a scuba diving mask by the support apparatus of the present invention.
Figure 6B:
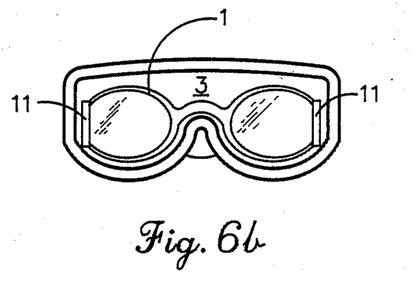
FIG. 6b is a front elevation of a frame-lens assembly of a conventional pair of eyeglasses suported within a protective "ski goggle" mask by the support apparatus of the present invention.
Figure 6C:
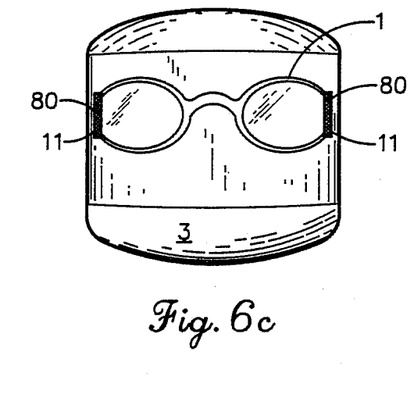
FIG. 6c is a front elevation of a conventional eyeglass frame and lens assembly supported on a protective face shield by the support apparatus of the present invention.
Figure 6D:
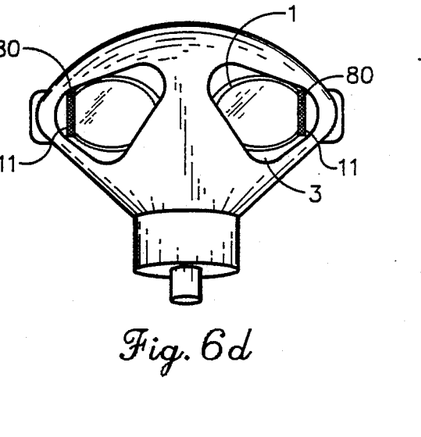
FIG. 6d is a front elevation of a frame and lens assembly of a conventional pair of eyeglasses supported within a gas mask by the support apparatus of the present invention.
Figure 7:
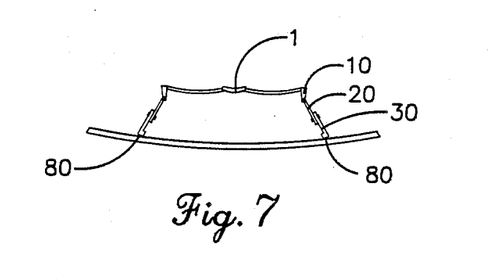
FIG. 7 is a plan view in section of a frame and lens assembly of a conventional pair of eyeglasses supported behind a protection face shield by first alternative embodiment of the support device of the present invention.

The exemplary preferred embodiment of FIG. 1 is particularly suitable for use in combination with face masks such as scuba diver masks and ski-goggle masks, as shown in FIG. 6a and 6b, where the viewing window of the mask and shroud or perimeter portion of the mask form an acute angle at the perimeter of the window on the interior of the mask. Where this interior angle of a mask is 90 degrees, or an obtuse angle, the support structure may not be retained satisfactorily within the mask by the outward urging of support assemblies 101, 102 by bias springs 46, 47 when the mask is not being worn. In the case of open protective face shields, as illustrated in FIGS. 6c and 7, or in hooded masking devices, such as the gas mask shown in FIG. 6d, where there is not angular border at the view window perimeter, retention and positioning of frame assembly 1 may be unsatisfactorily even when the mask is being worn. An alternative embodiment of the invention for such applications as shown in FIG. 6c and FIG. 7 and includes a releasable hook and loop fastener to hold contact portion 12 of base ends 11 of support members 10 in contact with the interior surface of the viewing window. In this alternative exemplary embodiment, hood and loop fasteners are provided on bias ends 11, and adhesive backed hook and loop fastener strips are attached to the interior of face shield 1 to allow base 11 to be attached to the interior window surface. When such attachment means are utilized to maintain contact between the base ends 11 and the interior surface of the viewing window 1, the resilient bias of springs 46, 47 will nontheless remain present and provide comfort and adaptability during activity while utilizing the support divice in combination with the mask.

Figures 8, 10, 11, 12, 13A, 13B, 13C:
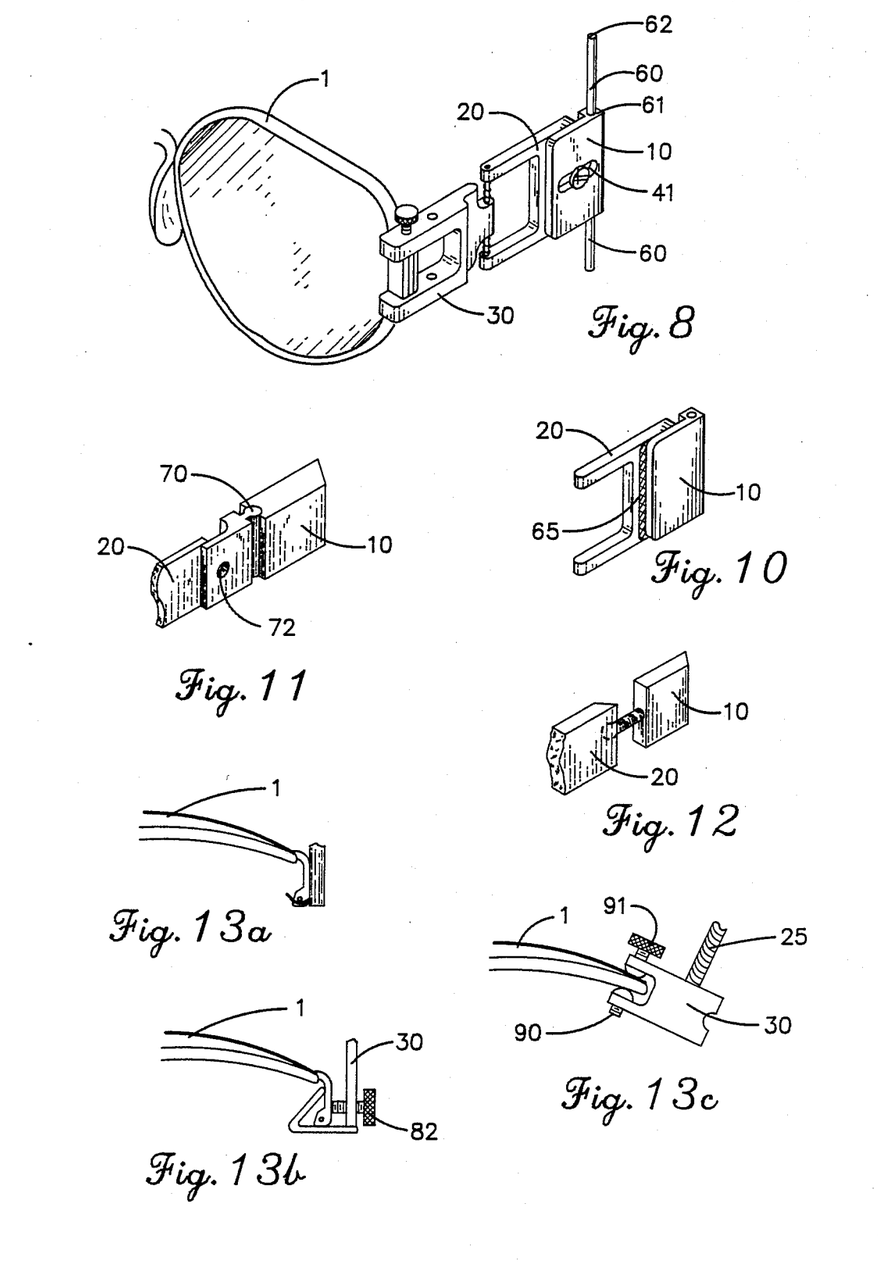
FIG. 8 is a perspective view of a support member with extensions of a second embodiment of the present invention.
FIG. 10 is a perspective view in which the support member and an adjustment member which are of a third embodiment of the present invention attached by means of a hook and loop fastener.
FIG. 11 is a perspective view of a support member and an adjustment member of fourth embodiment of the present invention attached by means of a dove-tail hinge.
FIG. 12 is a perspective view of a support member and an adjustment member of a fifth embodiment of the present invention attached by a socket and ball mounted in a screw extension.
FIG. 13a is a plan view showing a conventional eyeglass frame and lens assembly engaged by a clip engagement means of an adapter member of a sixth embodiment of the present invention.
FIG. 13b is a plan view of a conventional eyeglass frame and lens assembly engaged by a hinge clamping device on the engagement end of an adapter member of a seventh embodiment of the present invention.
FIG. 13c is a plan view of a conventional eyeglass frame and lens assembly engaged by a clamping device on the engagement end of an adapter member of a seventh embodiment of the present invention.

Another alternative embodiment for use in support situations where a mask may have a large viewing window, or where the window may have large perimeter radiuses or rectangular shapes, support members 10 may include extensions 60 at base ends 11, as illustrated in FIG. 8, which extend generally parallel to contact portion 12 of the base end 11 of support member 10, to contact the interior of mask shroud 4 or view window gasket 5 and assist in maintaining support members 10 in fixed relation with view window 3. Extensions 60 may be fabricated of a rigid material of appropriate length and inserted in apertures 61 formed in support members 10 to maintain the position of support members 10 by contact of extension ends 62 with mask shroud 4, or, as shown in an alternative embodiment of FIG. 9, extension 60 may be made of a spring material to bend against the interior of the mask shroud 4 and resiliently assist to maintain support members 10 properly positioned on the interior surface of view window 3. This allows extensions 10 of a single length to accommodate masks of various shapes and sizes. Thus, extensions 10 are preferably formed of a metallic coil spring material, preferably non-corrosive stainless steel, which may be covered with a vinyl layer to reduce chances of abrasion of shroud 4, but may be made of any suitably flexible and elastic metallic or non-metallic material.

Figure 9:
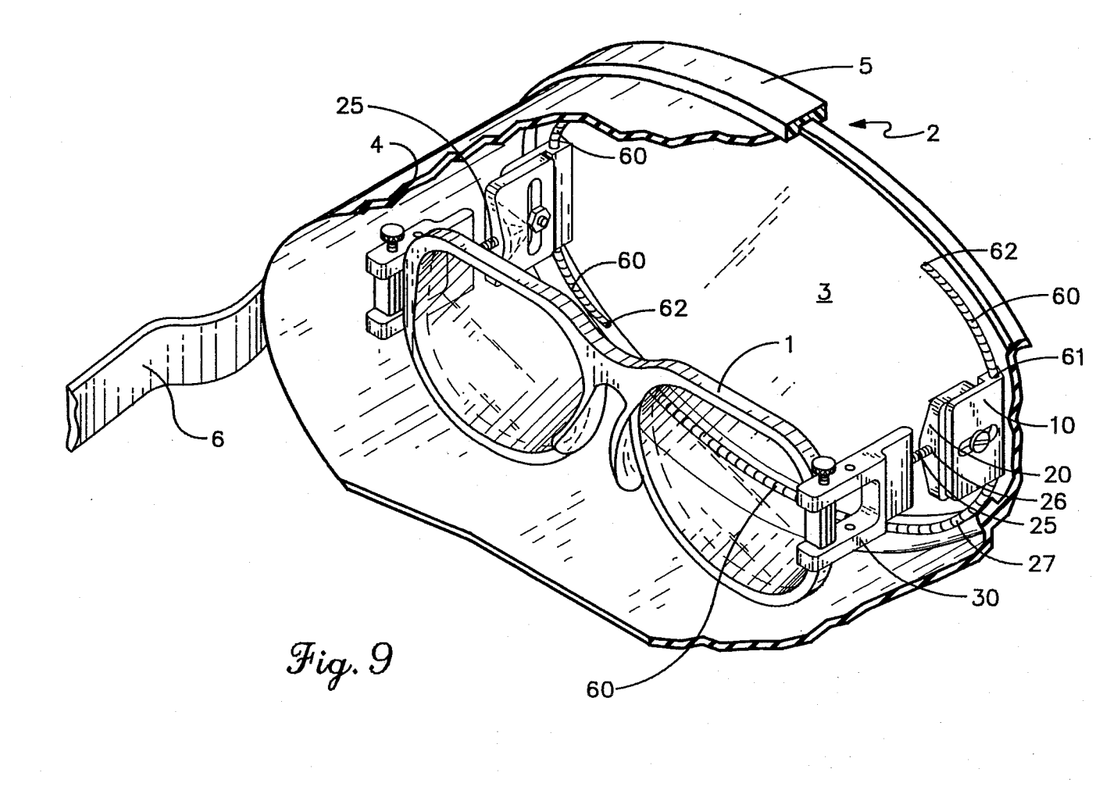
FIG. 9 is a partially cut away perspective view of a conventional eyeglass frame and lens assembly as it would be supported in a scuba mask by a support apparatus comprising an alternative embodiment of the present invention.

In an alternative embodiment of the frame assembly support apparatus of the present invention shown in FIG. 9, adapter members 30 are attached to support members 10 by coil springs 25, which bias support members 10 outwardly against shroud 4 of mask 2 to resiliently support adapter members 30 and frame assembly 1. Apertures 26, 27 may be sized and internally threaded to engage the ends of coil spring 25 with adapter members 30 and adjustment members 20, respectively, and further allow the spacing of frame assembly 1 from window 3 to be adjusted by turning spring 25 in a turn buckle like manner.

Embodiments including exemplary alternative means for adjustably attaching the support and adjustment members are illustrated in FIGS. 9 through 11. In the embodiment of FIG. 9, support members 10 and adjustment members 20 are releasably attached in abutting relation by hook and loop fastener 65 to allow the support member 10 and adjustment member 20 to be released from one another and reattached in the desired adjusted relative relation. In another embodiment, illustrated in FIG. 11, most suitable for fabrication of plastic, a dove-tail joint 70, allowing horizontal rotation and linear vertical adjustment, is provided in combination with a pivotal joint 72 to allow relative adjustment of support member 10 and adjustment members 20 with two rotational and one linear degree of freedom while providing sufficient frictional resistance to their relative motion to retain them in the desired adjusted position once adjustment is completed. FIG. 12 shows yet another embodiment in which a socket is formed in one of the support member 10 or adjustment member 11 and a ball which mates within the socket is attached to the other member by a threaded rod. This arrangement allows adjustment of the relation between the adjustment member and support member by longitudinal extension and three degrees of rotational freedom. In this embodiment, the adjusted position of the members may be maintained by friction or set screws.

FIGS. 13a through c show alternative embodiments of the present invention having various exemplary means for engagement of the temple portion of the frame assembly at the engagement end of adapter members 30. FIG. 13a is a resilient clip device for engaging the outside surface of the hings mount of the conventional eyeglass frame assembly. FIG. 13b shows a clamping arrangement for engagement of the temple hinge portion of the frame assembly in abutting relation with the engagement end of the adapter member 30. FIG. 13c illustrates a clamp device 76 for engagement of a temple portion of the eyeglass frame assembly 1 at the engagement end of adapter member 30.

In the alternative exemplary embodiment of FIG. 9, the diameter and pitch of the thread of threaded portion 51 of pin member 50 may be selected to match the interior thread of apertures 30, 35 to increase the versatility of the adapter member 30 by allowing it to be converted to a clamping adapter member as illustrated in FIG. 13c. This is accomplished by removing coil spring 25 from the support end adjustment aperture 27 of adapter member 30 and threading coil spring 25 into one of apertures 36 in the upper extension portion 34. A mushroom-shaped cushioning element 90 is then placed in one of apertures 37 in lower extension portions 35 with the head to mushroom-shaped cushioning element 90 lying inside channel 33. A clamping screw 91 may then be threaded into an opposing aperture 36 in the upper extension portion 34, to complete the clamp assembly, and tightened against frame assembly 1 to engage the frame assembly 1. Clamp screws 91 and cushioning elements 90 are preferably made of nylon, but may be made of any suitably durable and elastic material.

While exemplary eyeglass frame assembly support apparatus embodying the present invention have been shown and described, it will be understood, of course, that the invention is not limited to these embodiments. Modification of the present invention may be made by those skilled in the art, particularly in light of the foregoing teachings. For example, a rubber rod, or member of some other suitably elastic rigid material may be used to attach the support members 10 and adjustment members 20 rather than the coil spring of the described alternative embodiment. It is therefore contemplated by the appended claims to cover any such modification which incorporates the essential features of this invention or encompasses the true spirit and scope of the invention.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. An apparatus for supporting a frame-lens assembly of a conventional pair of eyeglasses, having right and left temple portions, within a face mask for a period of temporary use in combination with the mask wherein the mask has a viewing window and a tubular shroud including a first surrounding edge that surrounds the viewing window and a second surrounding edge spaced from the first surrounding edge to form a surrounding sidewall, the eyeglass supporting apparatus comprising:
   left and right support members;
   left and right pivotal attachment means for pivotally attaching the left and right temple portions of the eyeglass frame assmbly to said left and right support members respectively;
   means for rotationally biasing said support members outwardly and away from one another to urge said left and right support members into abutting relation to the shroud and to the viewing window, thereby causing the eyeglass frame assembly to be supported in a functional position within the mask.

2. An apparatus for supporting an eyeglass frame assembly as in claim 1 incuding releasable temple portion engagement means comprising a resilient clip adapted to partially surround and resiliently engage and retain the temple portion of said frame assembly.

3. An apparatus for supporting an eyeglass frame assembly as in claim 1 in which said releasable temple portion engagement means comprises a screw clamp adapted to engage and retain the temple portion of said frame assembly.

4. An apparatus for supporting a frame-lens assembly of a conventional pair of eyeglasses, having right and left temple portions, within a face mask for a period of temporary use in combination with the mask by a diver, the mask having a viewing window and a tubular resilient shroud including a first end surrounding and sealingly engaging the viewing window and a second end including a contoured edge adapted to form a water tight seal when urged against the divers face, the eyeglass supporting apparatus comprising:
   left and right support members, each of said support members having a base end, each of said base ends including a contact portion for contacting an interior surface of the viewing window;
   left and right adjustment members, each of said adjustment members having an adapter support end;
   left and right adapter members, each of said adapter members including a support end and a frame assembly engagement end, said frame assembly engagement end of said left and right adapter members including left and right means for releasably engaging the left and right temple portion of the frame assembly, respectively;
   means for attaching the support end of said left and right adapter members to the adapter support end of said left and right adjustment members, respectively; means for adjustably fastening said left and right adjustment members to said left and right support members, respectively, such that said left and right adjustment members may be fixed in an adjusted relation to said left and right support members to cause the frame assembly to be supported in a useful position within the mask when said left and right temple portions of the frame assembly are engaged by said left and right temple engagement means, respectively, said contact portions of said left and right support member base ends are in contact with the interior surface of the viewing window and the face mask is urged against the divers face.

5. An apparatus for supporting a frame assembly of a pair of eyeglasses as in claim 4, wherein said adjustable fastening means comprises clamping means whereby said support member and said adjustment member may be clamped in variable rotational and two-dimensional abutting relation, one to the other.

6. An apparatus for supporting eyeglasses as in claim 4 wherein said adjustable fastening means comprises an elongate channel through said support member, an elongate channel passing through said adjustment member, a retaining means including a shaft passing through both said support member channel and said adjustment member channel, said retaining means having end portions adapted to retain said support member and said adjustment member in an abutting relation with a longitudinal axis of said support member channel and a longitudinal axis of said adjustment member channel so oriented, one to the other, as to allow rotational and two-dimensional linear adjustment of said adjustment member relative to said support member.

7. An apparatus for supporting a frame assembly of a pair eyeglasses as in claim 4 wherein said adjustable fastening means comprises a hook and loop fastening means.

8. An apparatus for supporting a frame assembly of a pair of eyeglasses as in claim 4 wherein said adjustable means includes a lockable ball and socket device.

9. An apparatus for supporting a conventional eyeglass frame-lens assembly as in claim 4 wherein said support end of said adjustment member is shaped to define a "C" shaped opening, said support end of said adapter member surrounds an aperture running therethrough, and said apparatus further comprises a shaft mounted transversely across an open mouth of the "C" shaped opening, said shaft passing through said aperture.

10. An apparatus for supporting a conventional eyeglass frame assembly as in claim 9, in which said shaft and said aperture are sized relative to one another to provide a sliding fit, said support end of said adapter member is smaller that said open mouth, and said apparatus further comprises resilient biasing means for resiliently biasing said support end of said adapter member to a central position on said shaft, within said open mouth.

11. An appartus for supporting a conventional eyeglass frame assembly as in claim 10, in which said biasing means comprises a first and second partially compressed coil spring surrounding said shaft, said first and second spring separated by said support end of said adapter member.

12. An apparatus for supporting a conventional eyeglass frame assembly as in claim 10, in which said coil springs further resiliently, rotationally bias said left and right adjustment members outward and away from one another when said left and right temple portions of the frame assembly are engaged by said left and right temple engagement means, respectively.

13. An apparatus for supporting a conventional eyeglass frame assembly as in claim 4 in which said support end attachment means comprises a dove-tail style hinge.

14. An apparatus for supporting a frame assembly of a pair of eyeglasses as in claim 4, further comprising resilient biasing means for urging said left and right support members outwardly and away from one another and against the resilient shroud.

15. An apparatus for supporting an eyeglass frame assembly as in claim 14 in which said support members include extensions, said extensions extending outwardly to contact the resilient shroud thereby maintaining said support members properly located within the shroud.

16. An apparatus for supporting an eyeglass frame assembly as in claim 4, in which said releasable temple portion engagement means includes clamping means for clamping said temple portion of said frame assembly in abutting relation to said engagement end.

17. An apparatus for supporting an eyeglass frame assembly as in claim 4, in which said releasable engagement means includes a pin member adapted to pass through a hole in a hinge fitting of the temple portion of said frame assembly.

18. An apparatus for supporting an eyeglass frame assembly as in claim 17, in which said engagement members include an upper and lower extension portion defining an open channel therebetween, said upper and said lower extension portion each having an aperture, said apertures having a common axis and sized to retain said pin member, whereby the hinge fitting may be inserted into said channel and said pin may be inserted through said apertures and the hole in said hinge fitting.

19. An apparatus for supporting an eyeglass frame assembly as in claim 18, wherein at least one of said apertures and said pin include matable threads whereby said pin may be threadably retained within said aperture.

20. An apparatus for supporting a frame assembly of a pair of eyeglasses as in claim 4, wherein said support end attachment means comprises a coil spring.

21. An apparatus for supporting a frame assembly of a pair of eyeglasses as in claim 20, wherein said coil spring coils about a longitudinal axis running between a first end of said spring and a second end of said spring and said first end is fixed to said adapter member support end and said second end is fixed to said adjustment member support end.

22. An apparatus for supporting a frame assembly of a pair of eyeglasses as in claim 21, in which said adapter member support end defines a threaded aperture, said threaded aperture sized and pitched to receive said coil spring in threaded engagement.

23. An apparatus for supporting an eyeglasses frame assembly as in claim 21, in which said releasable engagement means includes a pin member adapted to pass through a hole in a hinge fitting of the temple portion of said frame assembly.

24. An apparatus for supportiong an eyeglass frame assembly as in claim 23, in which said engagement members include an upper and lower extension portion defining an open channel therebetween said upper and said lower extension portions each having an aperture, said apertures having a common axis and sized to retain said pin member, whereby the hinge fitting may be inserted into said channel and said pin may be inserted through said apertures and the hole in said hinge fitting.

25. An apparatus for supporting an eyeglass frame assembly as in claim 24, wherein said upper extension portion aperture and said pin include matable threads whereby said pin may be threadably retained within said aperture.

26. An apparatus for supporting an eyeglass frame assembly as in claim 25, wherein said threads of such upper extension portion aperture and said threads of said support end aperture are each sized and pitched to received said coil spring in threaded engagement.

27. An apparatus for supporting an eyeglass frame assembly as in claim 26, further comprising a mushroom-shaped cushion element with a pin portion and an enlarged head portion, said pin portion sized to be matable inserted in said lower extensions portion aperture.

28. An apparatus for supporting a conventional eyeglass frame-lens assembly for a period of temporary use in combination with a protective mask having a viewing window portion by a person wearing the mask, said support apparatus comprising:

left and right support members, each of said support members having a base end adapted to contact the interior surface of the viewing window portion;

left and right adjustment members, each of said adjustment members having an adapter support end;

left and right adapter members, each of said adapter members having a support end and a frame assembly engagement end, each of said frame assembly engagement ends including means for releasably engaging a temple portion of the frame assembly;

means for attaching the support end of said left and right adapter members to the adapter support end of said left and right adjustment members, respectively; and means for adjustably fastening said left and right adjustment members to said left and right support members, respectively, such that said left and right adjustment members may be fixed in an adjusted relation to said left and right support members whereby the frame and lenses are supported in a useful position relative to the person's eyes when said left and right temple portions of said frame assembly are engaged by said left and right engagement means, respectively, and said left and right base ends are in contact with the interior surface of the viewing window portion.

29. An apparatus for supporting a conventional eyeglass frame assembly as in claim 28 including means for releasably attaching each base end to the interior surface of the viewing window portion.

30. An apparatus for supporting a conventional eyeglass frame assembly as in claim 29, in which said releasable attachment means includes a hook and loop fastener.

31. An apparatus for supporting a conventional eyeglass frame assembly as in claim 29, in which said releasable attachment means includes surface adhesion means.

32. An apparatus for supporting a conventional eyeglass frame assembly as in claim 29, which said releasable attachment means includes a dove-tail key member affixed to the interior surface of the viewing window portion and a channel by said base end adapted to releasably retain said key member.

33. An apparatus for supporting a frame assembly of a pair of eyeglasses as in claim 28, wherein said support end attachment means comprises a coil spring.

34. An apparatus for supporting a frame assembly of a pair of eyeglasses as in claim 33, wherein said coil spring coils about a longitudinal axis running between a first end of said spring and a second end of said spring and said first end is fixed to said adapter member and said second end is fixed to said adjustment member.

35. An apparatus for supporting a frame assembly of a pair of eyeglasses as in claim 34, in which said adapter member defines a threaded aperture, said aperture sized to receive said coil spring in threaded engagement.

36. An apparatus for supporting a frame assembly of a pair of eyeglasses as in claim 34, in which said adjustment member defines a threaded aperture, said aperture sized and pitched to received said coil spring in threaded engagement.

37. An apparatus for supporting an eyeglass frame assembly as in claim 36, in which said releasable engagement means includes a pin member adapted to pass through a hole in a hinge fitting of the temple portion of said frame assembly.

38. An apparatus for supporting an eyeglass frame assembly as in claim 37 in which said engagement members include an upper and lower extension portion defining an open channel therebetween, said upper and said lower extension portion each having an aperture, said apertures having a common axis and sized to retain said pin member, whereby the hinge fitting may be inserted into said channel and said pin may be inserted through said apertures and the hole in said hinge fitting.

39. An apparatus for supporting an eyeglass frame assembly as in claim 38 wherein said upper extension portion aperture and said pin include matable threads whereby said pin may be threadably retained within said aperture.

40. An apparatus for supporting an eyeglass frame assembly as in claim 39, wherein said threads of said upper extension portion aperture and said treads of said support end aperture are each sized and pitched to receive said coil spring in threaded engagement.

41. An apparatus for supporting an eyeglass frame assembly as in claim 40, further comprises a mushroom-shaped cushion element with a pin portion and an enlarged head portion, said pin portion sized to be matably inserted in said lower extension portion aperture.

* * * * *